US006431169B1

(12) United States Patent
do Val et al.

(10) Patent No.: US 6,431,169 B1
(45) Date of Patent: Aug. 13, 2002

(54) MINI PNEUMATIC MECHANICAL PULMONARY VENTILATOR

(75) Inventors: Humberto Ribeiro do Val; Wilson Valadao de Azeredo, both of Vitoria (BR)

(73) Assignee: Vent-Logos Sistemas Logicos S/A, Santal Luiza Victoria (BR)

( * ) Notice: Subject to any disclaimer, the term of this patent is extended or adjusted under 35 U.S.C. 154(b) by 0 days.

(21) Appl. No.: 09/454,630

(22) Filed: Dec. 3, 1999

(30) Foreign Application Priority Data

Aug. 5, 1999 (BR) .............................................. 9903858

(51) Int. Cl.[7] ............................................ A61M 15/00
(52) U.S. Cl. ................................................ 128/200.24
(58) Field of Search ...................... 128/200.24, 204.18, 128/204.21, 204.23, 204.24, 204.25, 204.26, 205.16, 205.18, 205.24

(56) References Cited

U.S. PATENT DOCUMENTS

| 3,918,447 | A | * | 11/1975 | Inkster et al. ............. 128/145.8 |
| 4,592,349 | A | * | 6/1986 | Bird ....................... 128/204.25 |
| 4,823,787 | A | * | 4/1989 | Adhan .................... 128/203.27 |
| 5,183,038 | A | * | 2/1993 | Hoffman et al. ........ 128/204.21 |
| 5,211,171 | A | * | 5/1993 | Choromokos ........... 128/205.19 |
| 5,222,491 | A | * | 6/1993 | Thomas .................. 128/205.13 |
| 5,398,676 | A | * | 3/1995 | Press et al. ............. 128/204.23 |
| 5,452,713 | A | * | 9/1995 | Vipond et al. .......... 128/204.18 |

* cited by examiner

Primary Examiner—John G. Weiss
Assistant Examiner—Teena K Mitchell
(74) Attorney, Agent, or Firm—Merchant & Gould PC

(57) ABSTRACT

The present invention discloses a pneumatic, mechanical, pulmonary ventilator apparatus. The apparatus operates to dilute and limit the pressure of various gases delivered to a patient. The function of the apparatus may be described as an astatic multi-vibrator, which is activated by pressurized gas (e.g., such as oxygen or medical compressed air). The gas output of the apparatus may be described as a square wave, wherein the high wave phase corresponds to the inspiratory phase (the duration is the inspiratory time) and the low wave phase corresponds to the expiratory phase (the duration is the expiratory time). The sum of the two phases corresponds to the respiratory cycle. The device includes a rubber diaphragm having a ring shape to cyclically block a gas source aperture inlet. An adjustable needle valve, which controls the gas pressure in a small chamber on the opposite side of the diaphragm, together with a helical spring provide for tuning the two cycle phases. A venturi system limits the delivered pressure of gas to the patient and remains open during all cycles, thereby enabling the patient to breath independent of the cycle of the apparatus.

6 Claims, 40 Drawing Sheets

28

31

MINI PNEUMATIC MECHANICAL PULMONARY VENTILATOR

Figure 1:
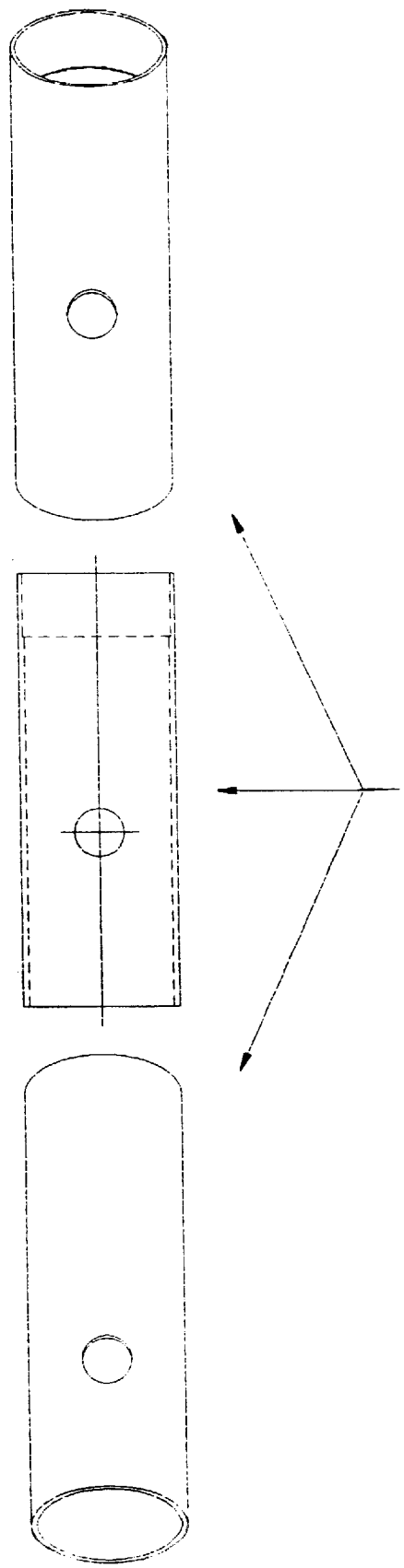

The present invent refers to an equipment destined to artificial ventilation in cases of respiratory insufficiency.

Pulmonary Ventilators are widely used in hospitals and related places. Due to the complexity of such device, they present high cost in reason of their constructive complexity, thereby limiting its acquisition to a larger number of users.

The Mini Pneumatic Mechanical Pulmonary Ventilator differs from the others, not in its purpose but in its practical aspect, which is based primarily in its constructive and operational simplicity. Its low cost also allows its acquisition both by entities and professionals that previously were unable to afford such and important equipment. The advent of such device will enable a larger number of professionals and health services to have access to an artificial ventilator that facilitates the transportation of patients and their care on the streets. It also completes the emergency units and can be used for the transportation of patients inside hospitals since it advantageously substitutes the manual lung ventilation, releasing therefore, the professional for other activities during an emergency.

Such device has the characteristic of liberating a high flow (around 90 liters/minute), allowing at the same time, restrict the air-way pressure (limited to 25 cm of water). This is a modern concept of lung ventilation denominated PCV (Pressure Control Ventilation). In practice there is an automatic flow adjustment due to pulmonary volume and air-way resistance that adequates the gas distribution impedance. Once the 25 cm of water pressure is reached, the flow is interrupted in the units which the pressure has entered in equilibrium with the generated pressure of the device, leaving a residual flow in the units which have not yet been filled, therefore reducing significantly the possibility of a pulmonary rupture (volutrauma or barotrauma).

Among other features this equipment also presents:

operation facility since it has just one control (frequency)

low consumption of gas (2,5 liters/minute for any age given group), which guarantees great autonomy;

small size;

low cost;

robustness;

safety usage: the VENTURI system which is used to dilute oxygen, limits the pressure of the air-way and remains opened during all respiratory cycle, enabling patient to breath independently and regardless of the device cycling.

Basically, the Mini Pneumatic Mechanical Pulmonary Ventilator is an astatic multi-vibrator, activated by conventional sources of pressurized gas such as oxygen or medical compressed air.

For the construction of pulmonary ventilators, multi-vibrators are used to generate square wave. In a ventilator, the high wave phase corresponds to the inspiratory phase and its duration is called inspiratory time. The low phase corresponds to the expiratory phase and its duration is called expiratory time. The sum of those two times corresponds to a respiratory cycle and the unit of time (minute) divided by that period is defined as the respiratory frequency. Other parameter in artificial ventilation is the ratio between these two periods of time, denominated the inspiratory: expiratory ratio (I: E ratio).

The variation of the flow released in the inspiratory phase allows the volume control of the gas, which is introduced in the lung during inspiratory time. In order to avoid mechanic trauma in the lungs by excessive pressure, the ventilators must have a pressure controlling system.

In the Mini Pneumatic Mechanical Pulmonary Ventilator, such controls are simplified as follows:

flow—during the inspiratory phase a fixed flow goes through the injector which is amplified by the VENTURI system thus allowing its automatic adjustment, as previously described;

air-way pressure—the VENTURI system is designed in such a way as to limit the pressure to 25 cm of water;

I:E ratio—it is fixed in the range of 1:2 to 1:2.5 during the device assembling;

Control of respiratory frequency—this is the only control to be adjusted by the operator. In order to make the operation easier, pictures of a sucking baby, a child and an adult have been printed beside the frequency control knob and one should match the knob with the printed picture that the case indicates;

For a better understanding, the Mini Pneumatic Mechanical Pulmonary Ventilator shall be described based on the attached drawings hereto:

FIG. 1: a non-magnetic stainless metallic tube with the function to encapsulate the mechanism.

Figure 2:
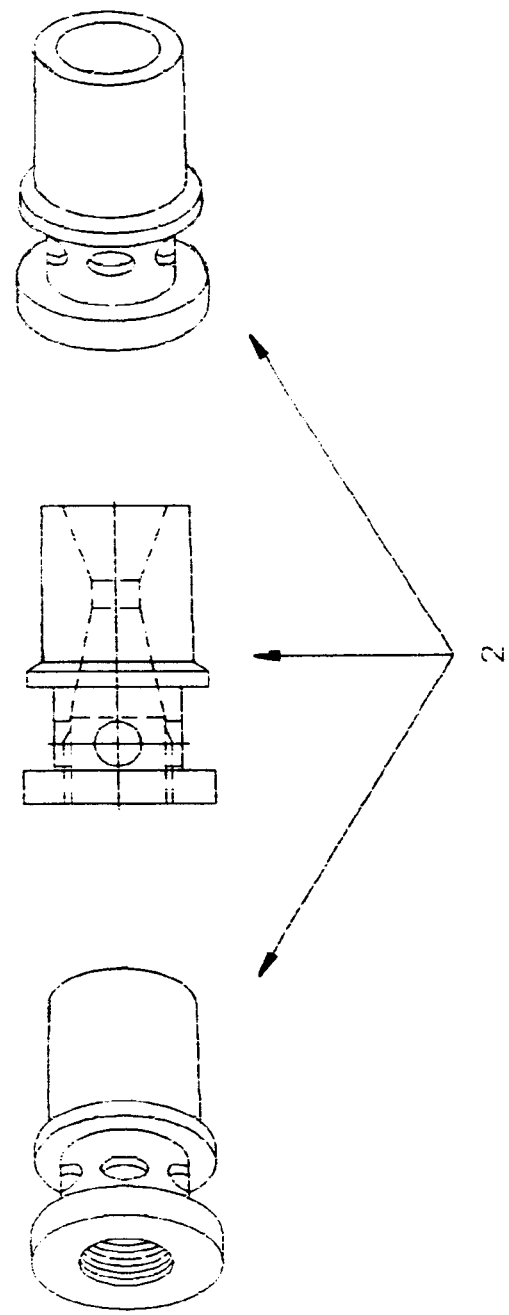
Figure 3:
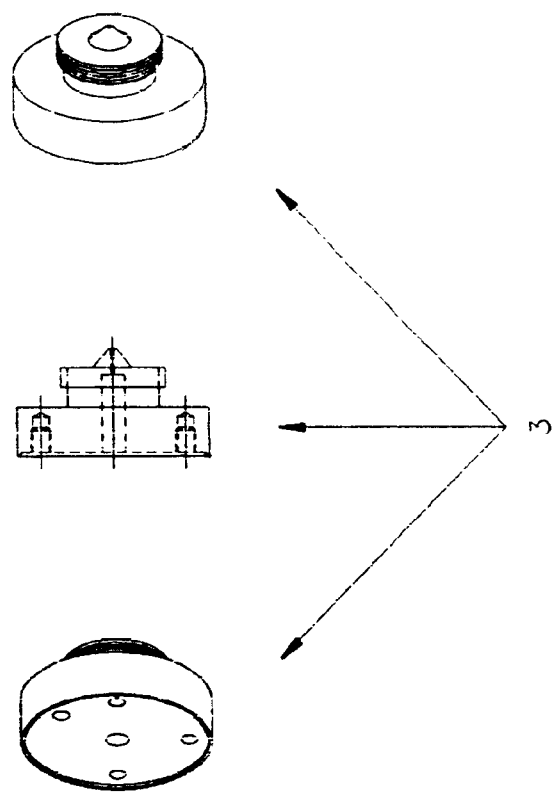

FIG. 2: a tubular component with one of its extremities showing an external cone (standard 22,0 mm) which adapts itself to the artificial air-way connection and the other, with an internal thread which adapts itself to the thread in the lower module as described in the FIG. 3. In its interior there is a conic hole (opening) which works as a VENTURI system diffuser. Near the upper extremity, there are perpendicular holes with the function to let the entrance of the environment air.

FIG. 3: a cylindrical module made of solid material, impermeable to the feeding gas, which works as the device base where it is fixed four wire rods which hold all the other modules. In its lower extremity a thread fixes the previously described component and in its middle, a 0,5 mm diameter hole works as a VENTURI system injector.

Figure 4:
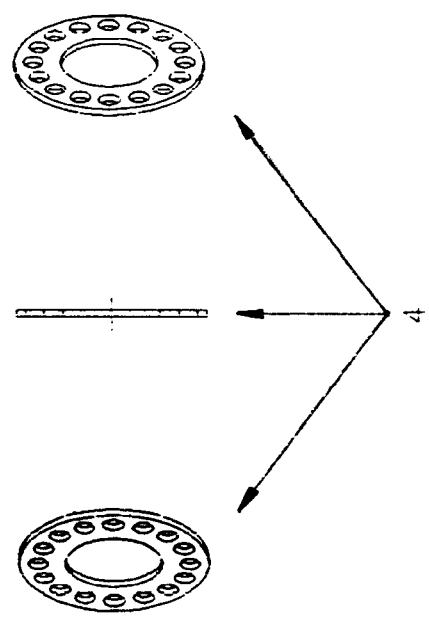

FIG. 4: a plain non-toxic rubber ring with the function to allow the hermetic coupling of the two modules with holes that permit their inter-communication whenever convenient.

Figure 5:
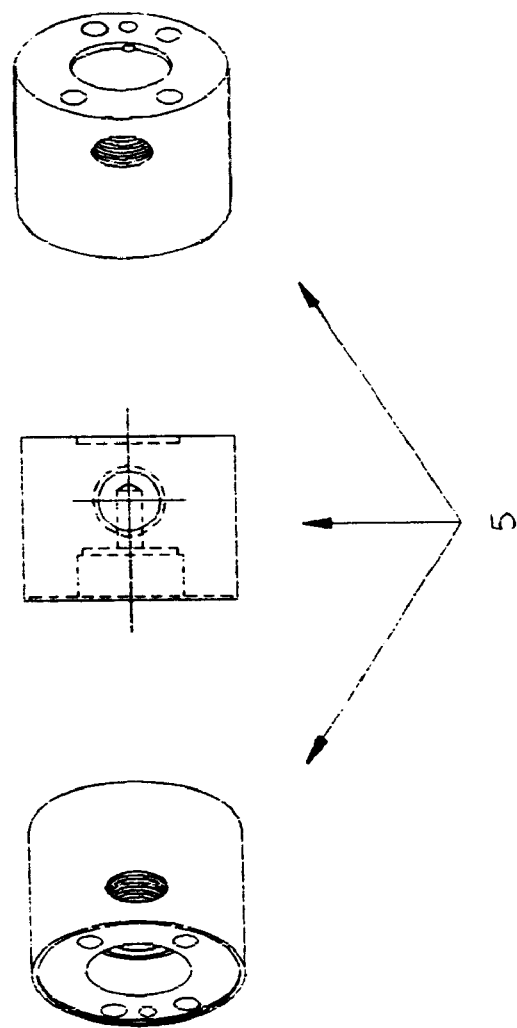
Figure 6:
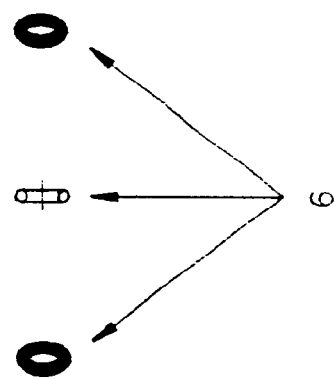

FIG. 5: a cylindrical module, built of solid material, impermeable to feeding gas, with a central cylindrical excavation in its upper surface where it lodges a sinter-bronze filter with the function to purify the gas that feeds the circuit device, that comes from the central hole which connects perpendicularly with the threaded hole in the lateral face of the module, where the feeding gas tube is connected. In its lower face there is a shallow depression where a connecting hole with a longitudinal hole with the same diameter of the wire rod holes which connects the equivalent hole, described in FIG. 19, that feeds the injector as described in FIG. 3. In a diameter of 21.0 mm, four holes with 2.5 mm diameter are found, through which pass the fixing wire rods, described in FIG. 24, FIG. 6: a cylindrical rubber blocking ring, non-toxic, "O-Ring" type.

Figure 7:
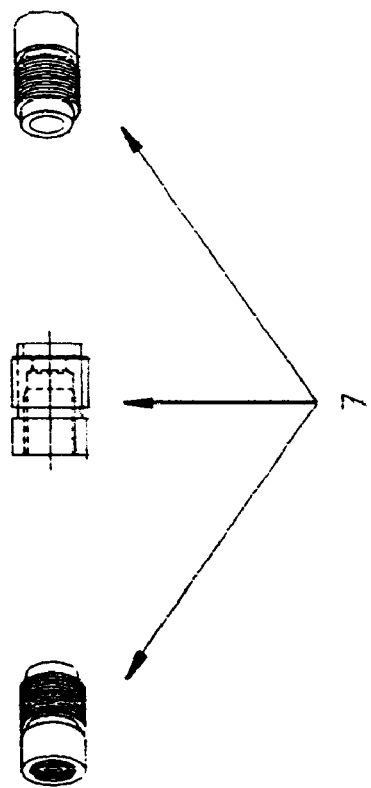

FIG. 7: a cylindrical module, build of solid material, non-toxic and impermeable to the feeding gas with an external thread in one of its extremities connected to the lateral threaded hole, as described in FIG. 5, and that has the function to fix all the components set to the external capsule. In this same extremity there is a small internal and flat lowering that adapts itself to the blocking ring, described in FIG. 6, and that has the function to block the connection of the metallic tube, described in FIG. 8, as well as to contact such component to the module, described in FIG. 5. In the other extremity there is an internal thread that adapts itself to a screw with a central hole that has the function of fixing the metallic tube where the flexible tube of the feeding system is connected.

Figure 8:
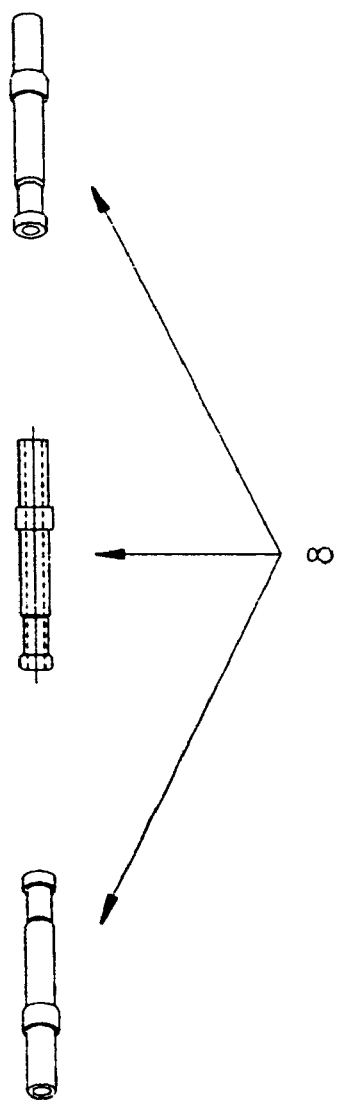

FIG. 8: a metallic tube, described in FIG. 7, where the flexible tube of the feeding system is connected.

Figure 9:
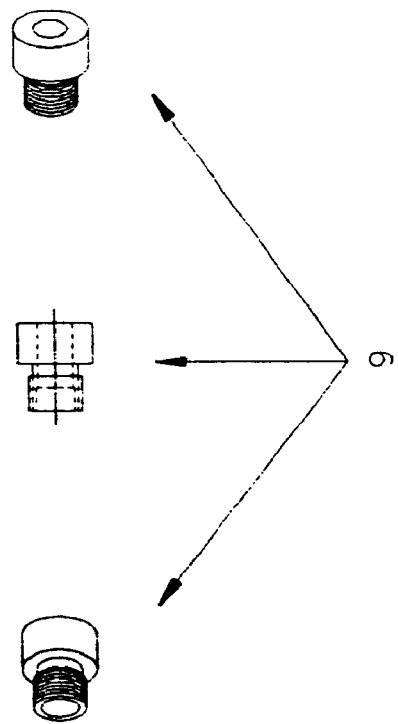

FIG. 9: a thread that has the function to fix the metallic tube, described in FIG. 8

Figure 10:
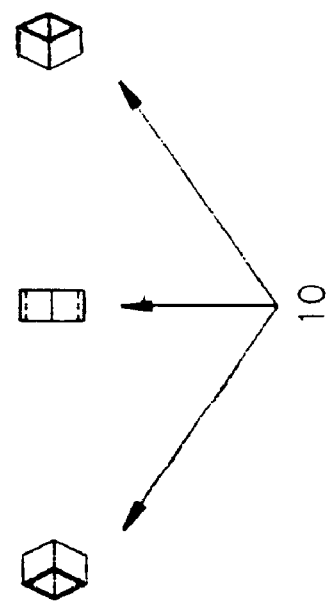

FIG. 10: a metallic staple that has the function to fix the feeding flexible tube to the metallic tube, described to FIG. 8

Figure 11:
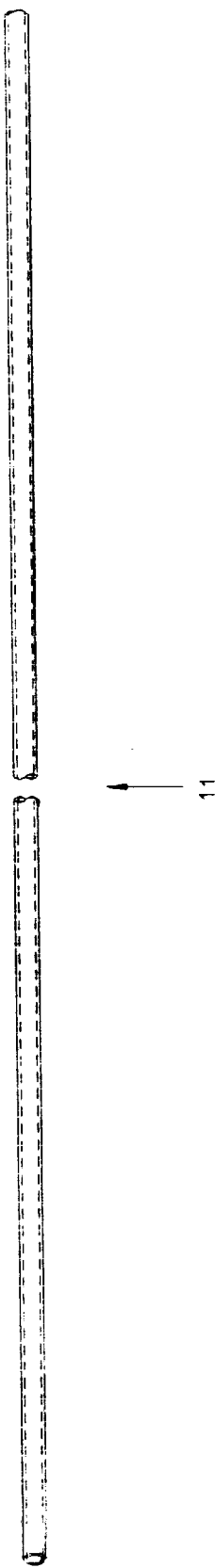

FIG. 11: a flexible tube that has the function to conduct the feeding gas to the system.

Figure 12:
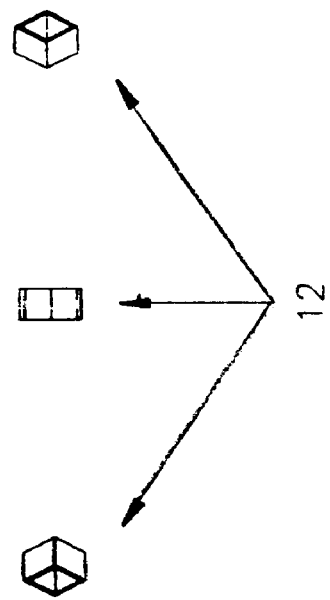

FIG. 12: a metallic staple, similar to that described in FIG. 10.

Figure 13:
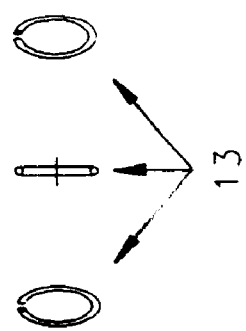
Figure 14:
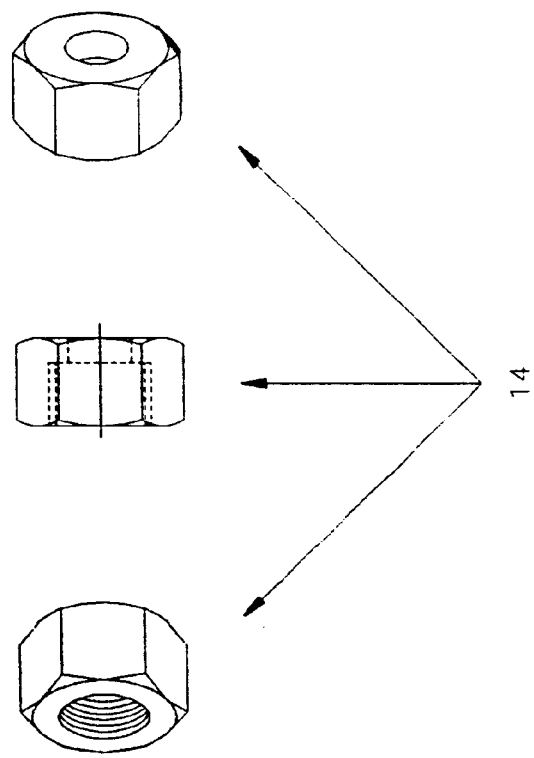
Figure 15:
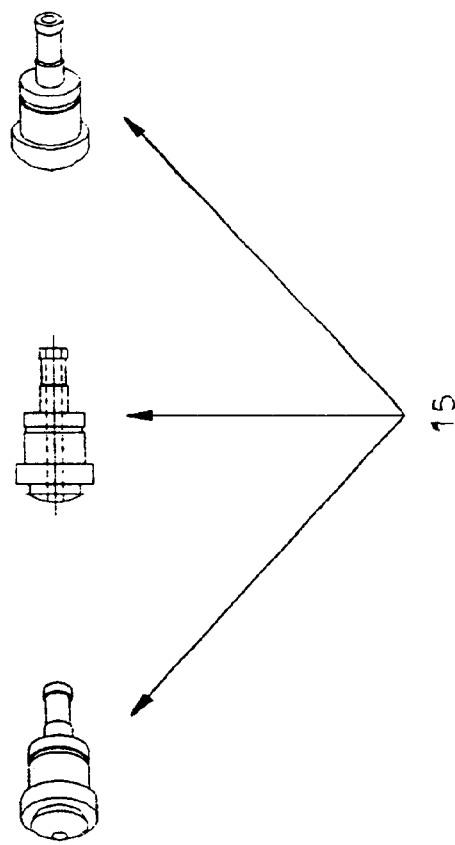

FIG. 13: a metallic ring that adapts to a furrow in the external lower part of the described component in FIG. 15 and that has the function to prevent the thread, as described hereunder in FIG. 14, from moving through the flexible tube, described in FIG. 11.

FIG. 14: a thread made of rigid material that has the function to fix the flexible tube to the feeding gas connection.

FIG. 15: a tubular component that in one of its extremities adapts itself to the flexible tube, described in FIG. 11, and at the other end, it has a furrow where a cylindrical rubber blocking ring, non-toxic—"O-Ring" type, that has the function to block such coupling with a gas plug source.

Figure 16:
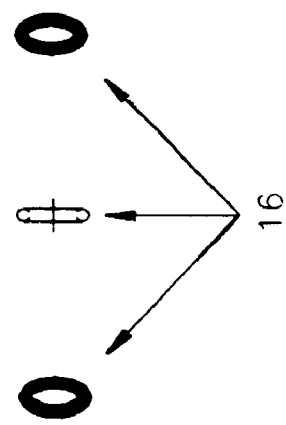

FIG. 16: a cylindrical rubber blocking ring, non-toxic—"O-Ring" type, described in FIG. 15.

Figure 17:
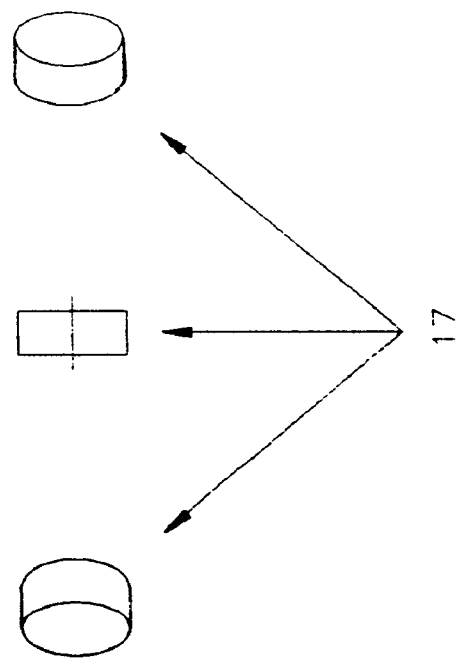

FIG. 17: a sinter-bronze filter, that has the function to purify the circuit feeding gas, described in FIG. 5.

Figure 18:
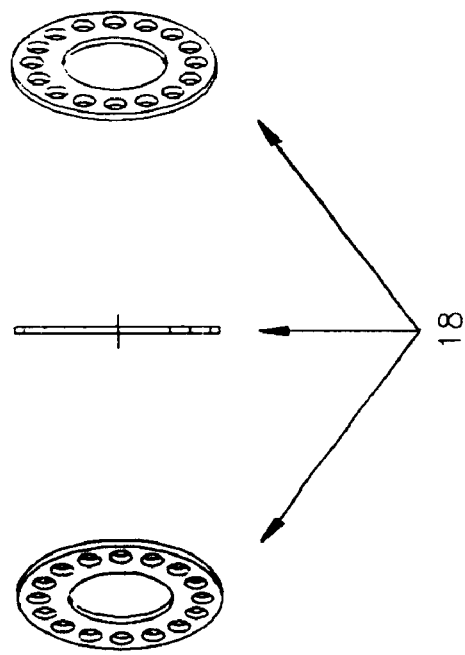

FIG. 18: a flat rubber ring, non-toxic, the same as described in FIG. 4

Figure 19:
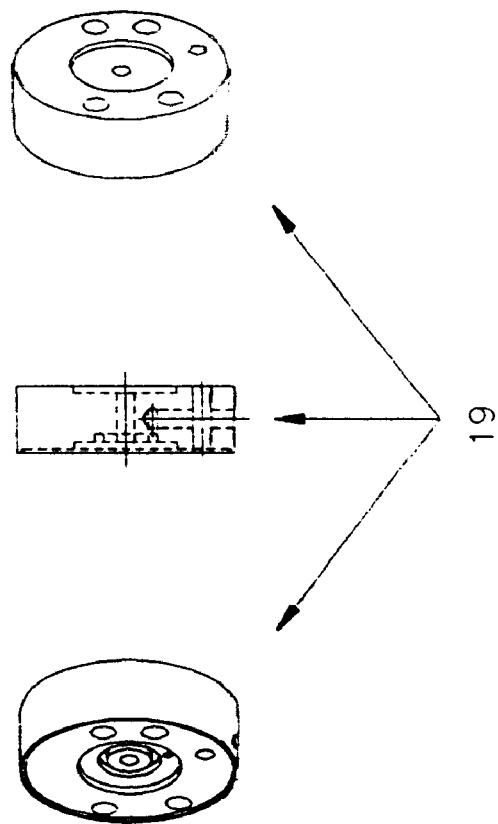

FIG. 19: cylindrical module of solid material impermeable to the feeding gas that in its upper face shows a flat cylindrical depression. In its 7.0 mm diameter, there is furrow where a hole opens up which is connected to a lateral hole in a 21.0 mm diameter and further connecting with the modules located in its upper and lower face. Such module has the function to conduct the gas into the direction of the needle valve and to the injector, described in FIG. 3. In the center of this module, there is a passing hole that conducts the gas coming from the sinter-bronze filter and that will be cyclically obstructed by the lower part ring of the diaphragm, described in FIG. 20. In its lower face it is found a cylindrical depression that lodges the upper part of the bronze sinter filter, described in FIG. 17. In a 21.0 mm diameter, there are four holes with a 2.5 mm diameter, through which pass the component set of fixing wire rods, described in FIG. 24.

Figure 20:
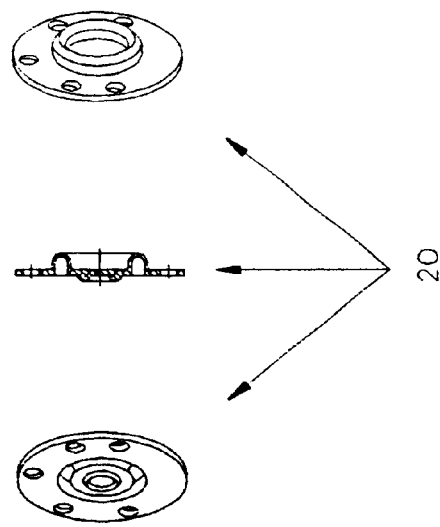

FIG. 20: a non-toxic rubber diaphragm with external ring equal to the rubber rings, described in FIGS. 4 and 18. In its central part there is a ring, with a concave shape, that has the function to enable the axial movement fom the central part, where in its lower face it is found a 6.0 mm diameter shape-ringed salience, "O-Ring" type, that has the function to block the central hole of the module, described in FIG. 19.

Figure 21:
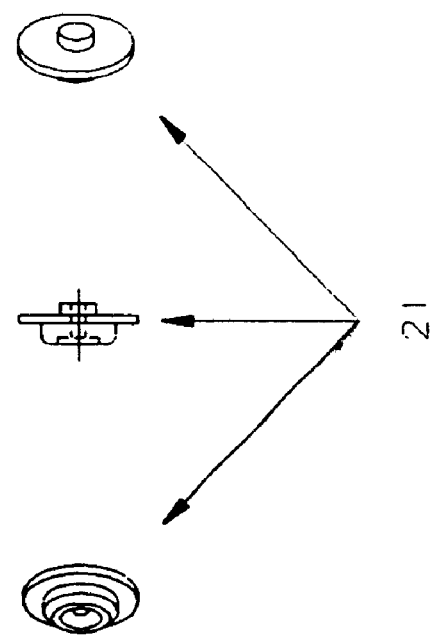
Figure 22:
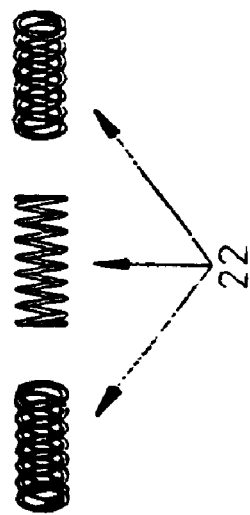

FIG. 21: a discoid component, built of solid material, that on its upper part shows a cylindrical projection, that has the function to fix the spring, described in FIG. 22 and in its lower face, designed so as to be compatible to its adaptation to the diaphragm upper face, described in FIG. 20.

FIG. 22: a helicoidal spring, steel built, that has the function to compress central part of the diaphragm, described in FIG. 20 so as to make the "O-Ring" type ring, described in the lower face of such diaphragm, block the central module hole, described in FIG. 19.

Figure 23:
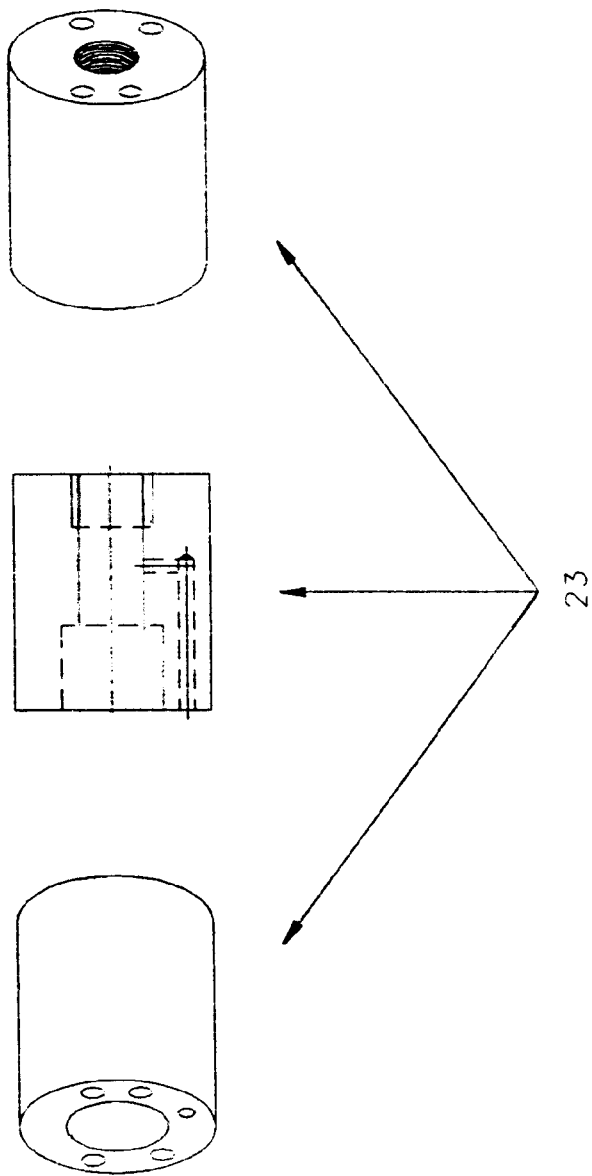

FIG. 23: a tubular cylindrical module, built with solid material impermeable to feeding gas presenting in its lower part a cylindrical excavation with a 15.5 mm diameter and 13.0 mm depth and that has the function to serve as a pneumatic condenser which is necessary for the time adjustment of the inspiratory and expiratory phases. In its upper part the central hole is threaded so as to fix the needle valve carcass, described in FIG. 27. In a diameter of 21.0 mm, there are four longitudinal holes with 2.5 mm of diameter, through which pass the fixing wire rods, described in FIG. 24. In its lower face with the same diameter, there is a longitudinal hole that couples with the equivalent hole of the described module in FIG. 19, with a 25.0 mm depth and that has the function to conduct the gas coming from the lateral hole, that has its origin in the furrow of the upper face of the module, described in FIG. 19, during the "turned on" phase of the device and to allow the decompression of its lower face chamber (above diaphragm). The middle part of the central hole accommodates the external blocking ring of the needle valve carcass, described in the same FIG. 27.

Figure 24:
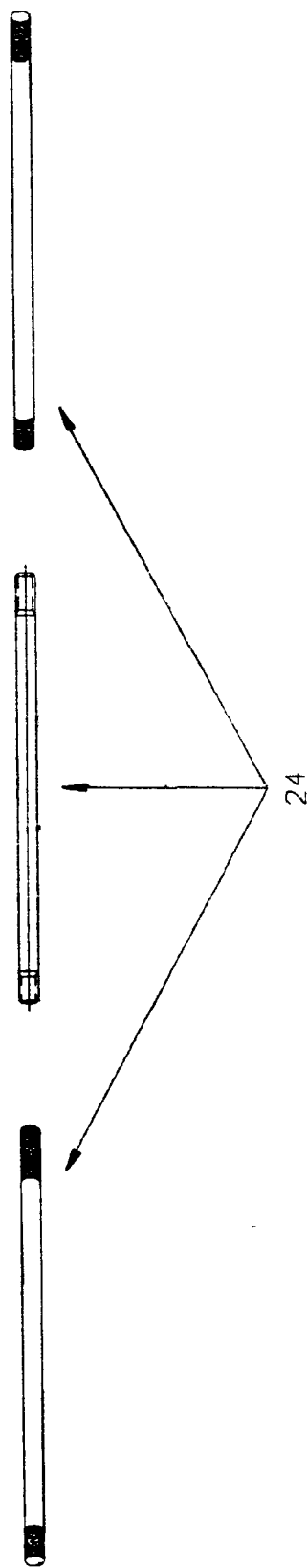
Figure 32:
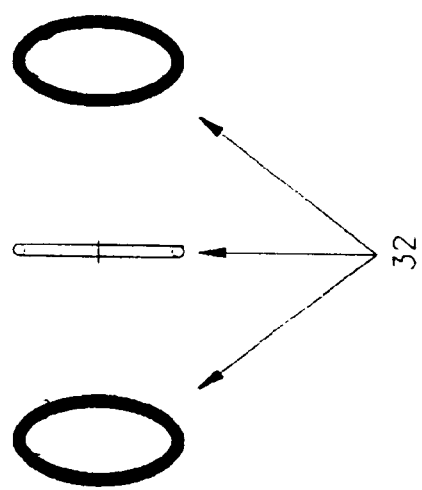

FIG. 24: four stainless steel rods (it can be of other material), non-magnetizing with a 2.00 mm diameter, three of them having a 69.0 mm length and one a 72.0 mm length, with the function to limit the course of the frequency regulator knob, described in FIG. 32.

Figure 25:
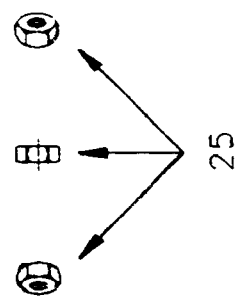

FIG. 25: four threads that adapt to the rods, described in FIG. 24, that has the function to fix all the device modules.

Figure 26:
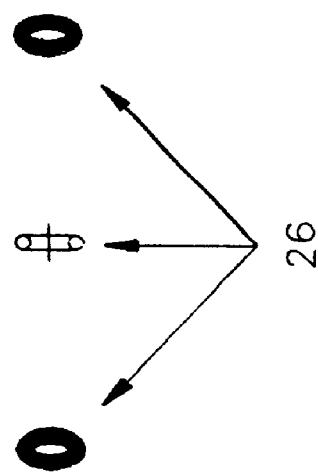

FIG. 26: two non-toxic blocking rings of cylindrical rubber adapted in their own furrrows in the in the external part of the needle valve carcass that has the function to block the segment of the same, at the point where the feeding gas comes through the lateral hole, described in the FIG. 23 module.

Figure 27:
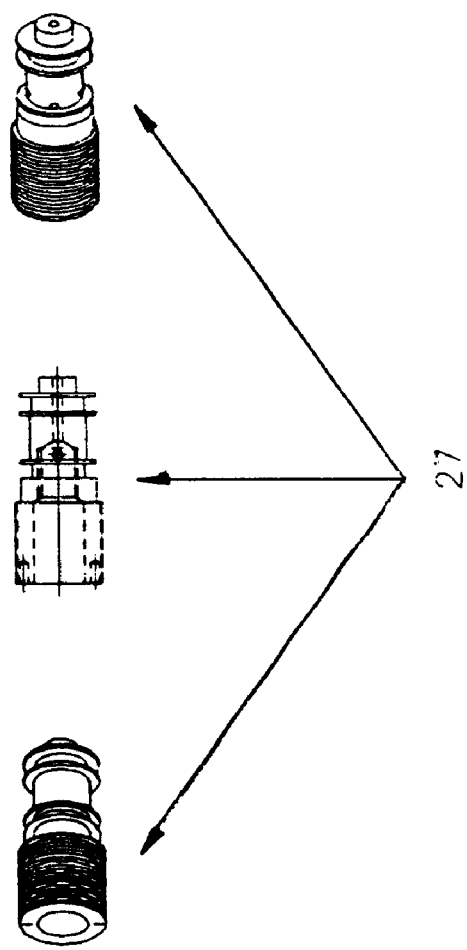

FIG. 27: a needle valve carcass, built of solid material, cylindrical shaped presenting two external furrows where the two blocking rings, described in FIG. 26 are adapted and in its upper half, a thread that adapts itself to the threaded hole, of the upper part, described in FIG. 23. In the inner part, there is a hole that adapts itself to the needle valve pin. The upper part of this has polished walls, where it is adapted the pin blocking ring, previously described; the middle part presents a thread, that is compatible to the thread found in the same pin and in its lower part, it is found the needle valve case. Between the furrows that lodge the external blocking, there is hole that opens up right above the needle valve case. The valve's function is to control the gas flow that defines the chamber pressurization that is situated in the lower-portion of the module, described in FIG. 22 and that in its turn defines the ratio between the inspiratory and expiratory time, which can be put into action over it through the two hole located in the superior face of this carcass.

Figure 28:
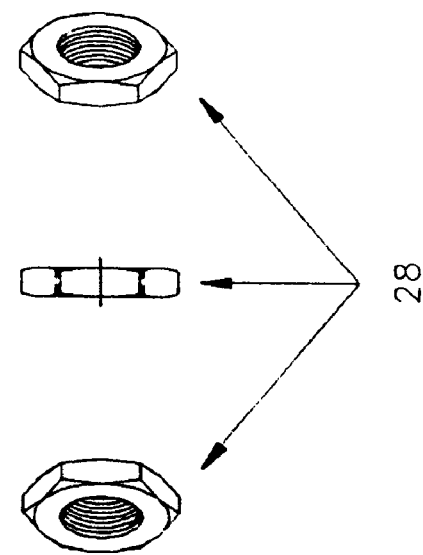

FIG. 28: a metallic thread, that adapts itself to the external thread of the component, described in FIG. 27 and that has the function to lock the carcass right after the adjustment of spring tension, described in FIG. 22.

Figure 29:
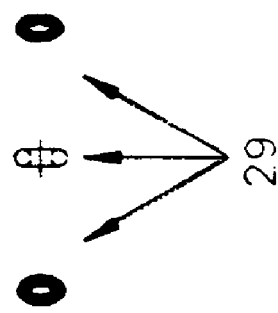
Figure 30:
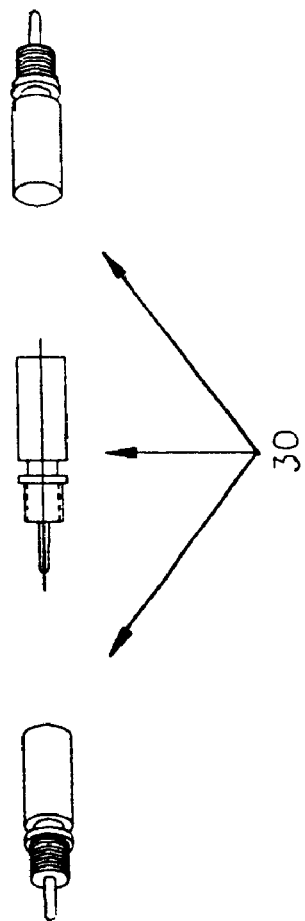

FIG. 29: a cylindrical rubber blocking ring, non-toxic that adapts itself in a proper furrow of the needle valve pin, described in FIG. 30 and that has the function, to prevent leakage of the gas that circulates through such valve.

Figure 31:
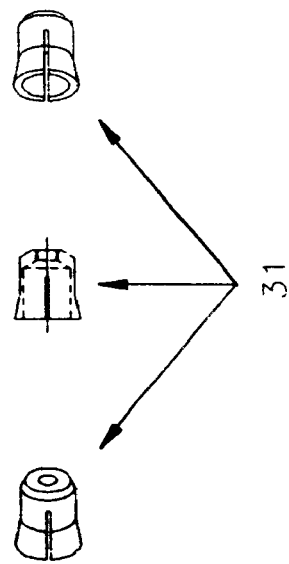
Figure 33:
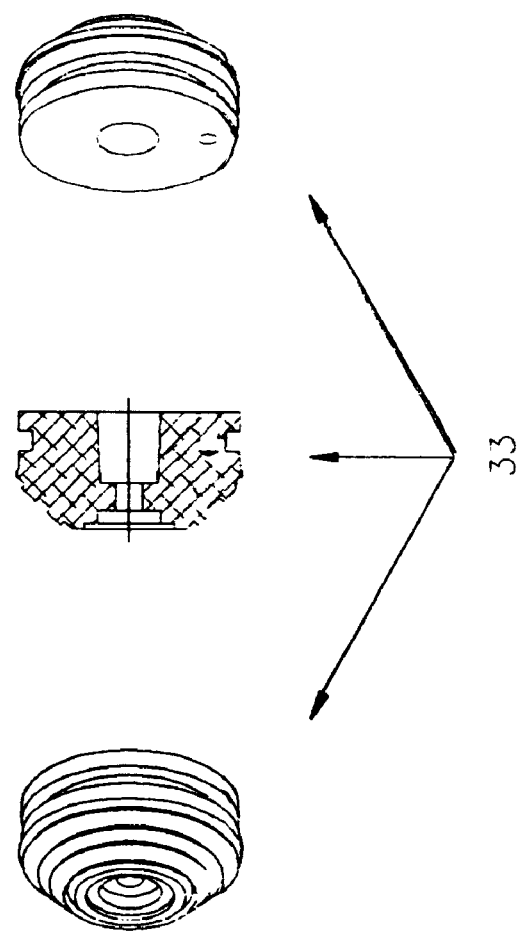
Figure 36:
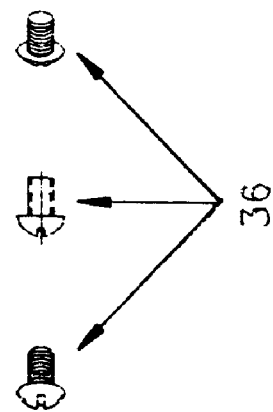

FIG. 30: a needle valve pin, built of solid material, which its upper part has 6.35 mm diameter (¼"), where it is fixed a frequency control knob, described in FIG. 33. Right below this section, there is a furrow that lodges a blocking ring described in FIG. 29. Below this furrow there is a thread, that adapts to the carcass internal thread, described in FIG. 27. In its lower extremity, it is located a conic spindle with a 1.45 mm diameter and 28' degree angle, that adapts to the lower part of the carcass case, described in FIG. 27 and that has the function to control the gas flow that defines the pressurization of the chamber located in the lower portion of the module, described in FIG. 23, in accordance to the description in FIG. 27;

FIG. 31: concave tweezers with 6.5 mm internal hole that adapts itself to the upper part of the needle valve pin, described in FIG. 30 and that fits to the center hole of the frequency control knob, described in FIG. 33, presenting in its lower part, two longitudinal cuts that have the function, to reduce the component's internal diameter, fixing it over the needle valve pin, when the screw is tightened, as described in FIG. 36 and that has the function, to fix the frequency knob of the needle valve pin.

FIG. 32: non-toxic cylindrical rubber blocking ring that has the function to define the circular motion tension of the frequency control knob.

FIG. 33: a cylindrical knob, built of solid material that has as its function the respiratory frequency control and that presents in its lower part a furrow where it is adapted to the blocking ring, as described in FIG. 32 and that has as function to limit the circular motion freedom of the frequency knob, with conic upper part and knurled, with a central hole, and that in its lower part, it is adapted to the conic tweezers, described in FIG. 31 and that in its upper part, it presents a cylindrical excavation that lodges the screw, described in FIG. 36 and a 12.0 mm diameter shallow cylindrical excavation, where it is adapted a finishing seal with an indication of the knob positioning. In its lower surface, there is a 21.0 mm diameter hole where it is lodged a cylindrical pin, described in FIG. 24 and that has as its function, to limit the bottom's angle rotation, leaning on the extremity of the longer rod.

Figure 34:
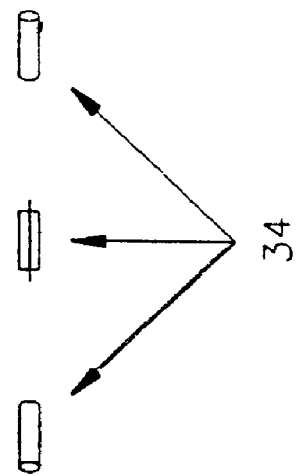

FIG. 34: a cylindrical pin, constructed of solid material that is lodged in a hole described in the bottom's lower surface, as described in FIG. 33

Figure 35:
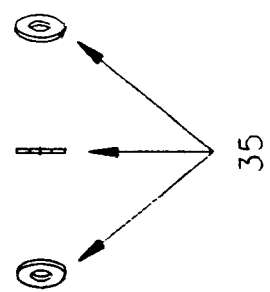

FIG. 35: a metallic washer that adapts itself to the screw of FIG. 36.

FIG. 36: a metal screw, with a 3.2 mm diameter and 6.0 mm length, with a slot in its head and that has the function to fix the frequency knob, a described in FIG. 33.

Figure 37:
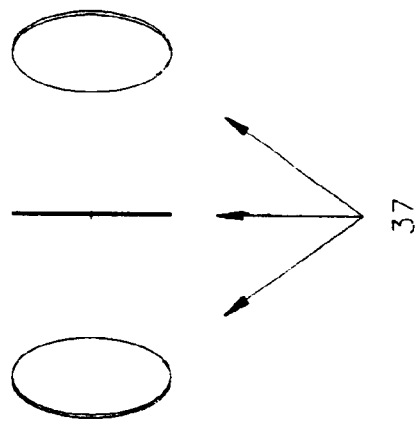

FIG. 37: seal of plastic material that presents in its upper surface, a picture to guide the positioning of the frequency control knob, described in FIG. 33.

Figure 38:
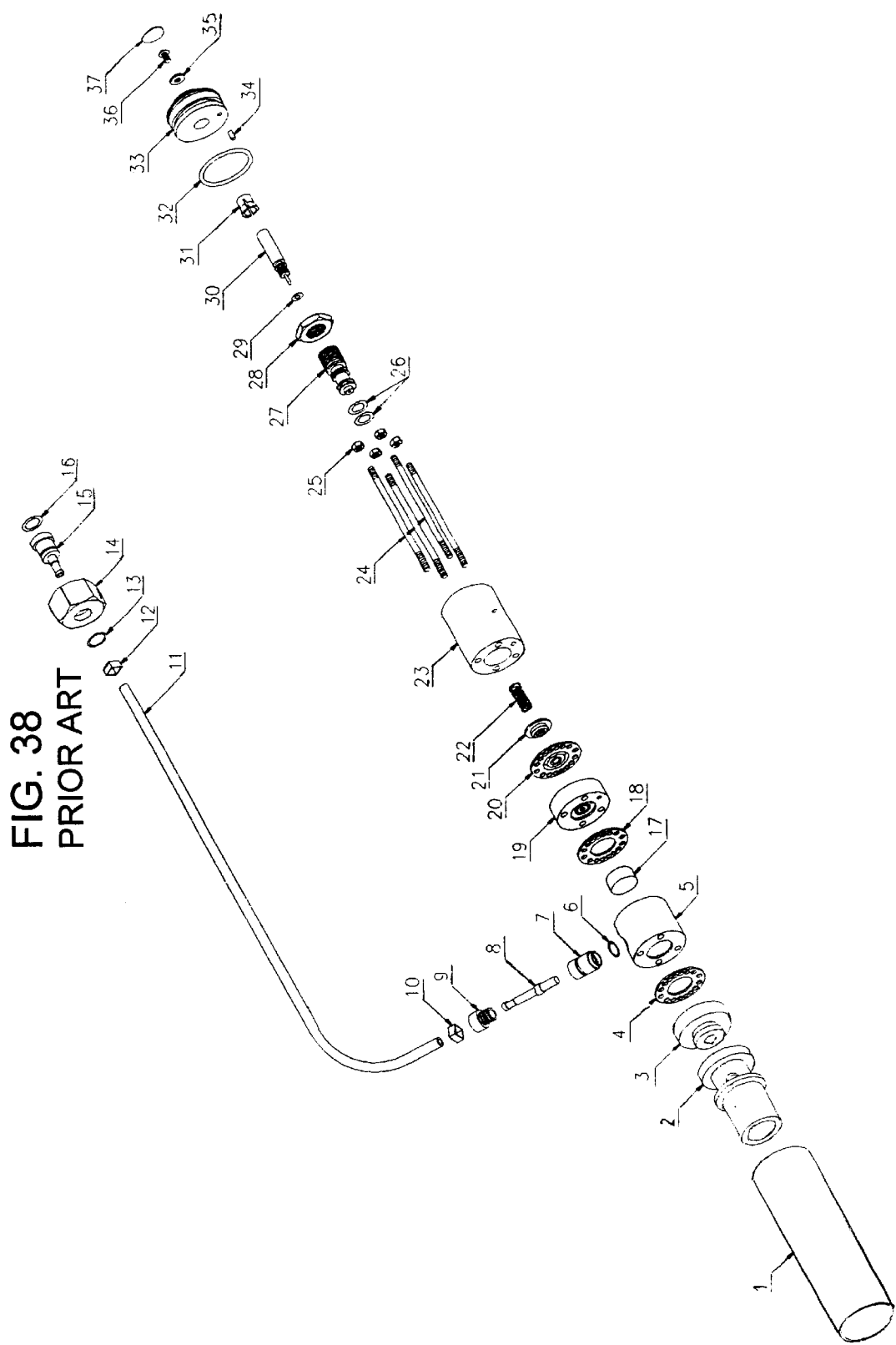

FIG. 38: exposed drawings of device's components in 3D.

Figure 39:
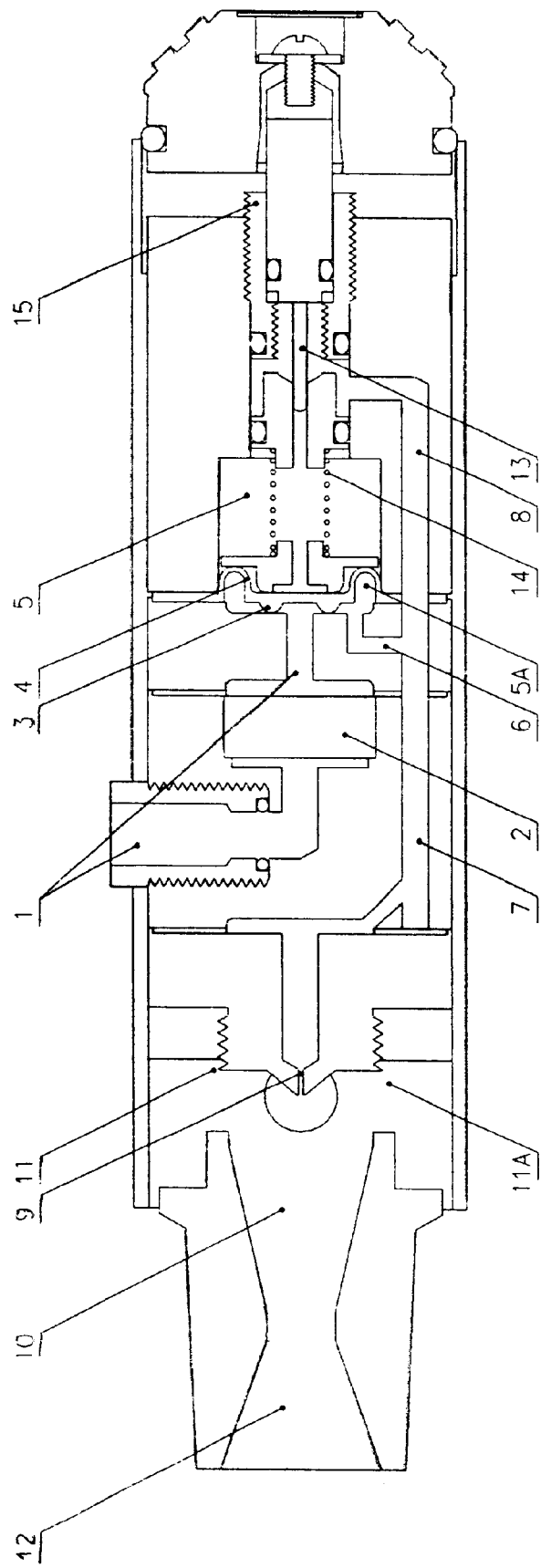

FIG. 39: device's sketched drawing.

Figure 40:

FIG. 40: device photography—"Mini Pneumatic Mechanical Ventilator"

WORKING MECHANISM OF THE MINI PNEUMATIC MECHANICAL PULMONARY VENTILATOR (FIG. 39)

A source of 50 psi or 3.5 kgf/cm$^2$ pressurized gas (Oxygen or Medicinal Compressed Air) is connected to the hole (1). The gas originating from such source goes through the filter (2) and proceeds in the direction of the ring shaped salience, "O-Ring" type (3) in the center of diaphragm (4), and moves towards the chamber (5), connecting the duct (1) to the duct (6). Thus, the gas that comes from (1) proceeds through the conduit (6) in two directions: a) conduit (7)—feeding the 0.5 mm diameter injector (9) that leads it to the diffuser (10) thus making that the surrounding air be aspirated through the holes (11 and 11a), generating up to 90 liter/minute of a mixture of air and oxygen in the outlet for the patient (12) and b) conduit (8)—to the needle valve (13) that controls its access to the chamber (5). When the pressure inside such chamber added to the spring tension (14), produces a higher strength than that which is exercised over the diaphragm by the chamber pressure (5A), it is forced downwards, thus making the ring-shaped center salience (3) to block the ring (1) finishing therefore the "turned on" phase, that corresponds the inspiratory phase and initiating the expiratory phase. Since no flow is left in (6) the gas that has been stored in the chamber (5) now goes in the opposite direction leaving slowly through the same needle valve (13) towards the surrounding air by the conduits (8,7 and injector 9).

With such gas leakage from chamber (5), its pressure drops progressively and when the power that is exercised over the diaphragm (4) added to the spring tension (14) is less than the that of the power exercised by the pressure of gas in the source over the area of ring shaped salience in the center of diaphragm (3), such gas escapes to the chamber (5A—below diaphragm), thus making that the power over it grows rapidly thereby raising it abruptly and connecting the ducts again (1) and (6), thus initiating a new inpiratory phase. Since the loading and the emptying of chamber (5) is carried out by the same valve (13) and since the loading pressure tends to be constant (pressure source) and the emptying drops continuously during the expiratory phase, the inspiratory time tends to be smaller than the expiratory one and it may be further adjusted to a longer or shorter period, in direct proportion to the spring (14) through the threaded component (15—needle valve carcass).

Due to what has been stated in this descriptive report, the following can be presented as advantages:

a) it may be conceived in a single set, of small size thus making it much more resistant and easy to be assembled, low production cost, with no empty spaces inside the device, where it normally accumulates debris or dust thereby causing contamination;

b) its mechanism is completely fabricated with very simple mechanical drawing components and materials that, despite its characteristics of durability, it has low cost and may be fabricated by revolution machining or by plastic or rubber molding thereby making its cost, again, very low;

c) the same mechanism works without moving components, with fine mechanical adjustment that makes it invulnerable to shocks. Since it has no moving attrition, the wearing off of its components is prevented, which increases its durability (working life) and makes it less liable to operational failure;

d) in the outlet it just has a VENTURI system that at the same time dilute the pure oxygen from the source, with the surrounding air to a mixture of 40% of $O_2$ and defines the maximum pressure in the air duct to 25 cm of water, what makes its use safe, concerning to barotraumas or toxicity of high $O_2$ concentrations;

e) It has just one control—the frequency, thus facilitating its use in emergencies, with no need of several adjustments by the user and enabling easiness in the handling, since it determines other ventilatory parameters within safety limits;

f) Low cost given its simple fabrication and assembling characteristics, making its acquisition possible all over the world, with the potentiality to fabricate it as a disposable device.

g) It should be taken into account its use in emergencies, since it has a "pneumatic" mechanism that uses as its activation source, the same pressurized gas that will be supplied to the patient, with no need of external energy sources such as batteries in which power failure would be extremely serious in the case of an emergency;

h) Reduced size and weight that could fit in an adult's palm thus facilitating its transportation together with a patient, regardless whether this transportation is carried out between hospitals or during the help of fire victims in burning buildings, for example. Its low weight and volume are helpful in the use of airplanes, helicopters and rescue planes or even, as an extra safety accessory, in regular flights, or in the armed forces, clubs, companies etc.

i) Flat cylindrical format with a stainless steel metallic capsule which facilitates tremendously its disinfection and conservation;

j) Very simple artificial air duct which can be constituted just by one tube, being recommended, however the use of a non-rebreathing valve.

k) Minimum internal complacence and artificial air duct, making it possible to be used in new born infants, children and adults;

l) It may be built from plastic materials and non-magnetizing metals, which makes it susceptible to be used in places with strong magnetic fields (in any spot of the room of magnetic nuclear resonance).

What is claimed is:

1. A mini pneumatic mechanical pulmonary ventilator comprising:

a single moving part, wherein the single moving part is a diaphragm including an outer edge, a flexible lateral part within the outer edge, and a ring-shaped salience formed on a first side of the diaphragm;

the ventilator having a gas inlet and a gas outlet, the gas inlet adapted to receive gas pressurized above ambient atmospheric pressure;

gas entering the ventilator through the gas inlet applying pressure to the first side of the diaphragm within the ring shaped salience, and a spring within a chamber applies pressure on a second opposing side of the diaphragm;

the pressure of the gas entering the ventilator from the gas inlet being sufficient to overcome the pressure of the spring and moving the diaphragm toward the chamber, opening a pathway for the gas to pass beyond the diaphragm;

the pathway allowing gas to move toward the gas outlet and toward a needle valve, the needle valve cooperating with a opening to allow some of the gas to leak past the needle valve and enter the chamber;

the pressure of the gas leaking into the chamber acting on the second side of the diaphragm, adding to the pressure being applied to the second side of the diaphragm by the spring until the pressure on the second side of the diaphragm is sufficient to move the diaphragm away from the chamber, blocking the pathway and holding the incoming gas from passing the diaphragm;

the gas within the chamber leaking past the needle valve out of the chamber into the passageway, reducing the pressure in the chamber until the pressure of the incoming gas within the ring-shaped salience on the first side is sufficient to move the diaphragm toward the chamber and allow gas from the gas inlet to enter the pathway;

a period of time when the pathway is closed to gas from the gas inlet defining a first cycle phase, and a period of time when the pathway is open to gas from the gas inlet defining a second cycle phase, the first and second phases together defining a cycle.

2. The mini pneumatic mechanical pulmonary ventilator of claim 1, wherein the ventilator includes a single diaphragm, the spring is a helicoidal spring, the chamber is about 2.5 cm$^3$ in volume, and a single needle valve controls the frequency of the phases on the cycle, the frequency of the phases determined by the rate of leakage of gas into and out of the chamber past the needle valve.

3. The mini pneumatic mechanical pulmonary ventilator of claim 2, wherein a ratio of the phases of the cycle is determined by the amount of pressure applied by the spring acting on the second side of the diaphragm and wherein the amount of pressure applied by the spring can be varied by the adjusting the depth of penetration of a threaded needle valve carcass into the chamber, the needle valve carcass threadably received within the ventilator and acting on a side of the spring away from the second side of diaphragm and the needle valve threadably received within the needle valve carcass.

4. The mini pneumatic mechanical pulmonary ventilator of claim 3, wherein the ventilator is contained within a unitary housing and the housing provides protection to the ventilator against falls or other physical impact.

5. The mini pneumatic mechanical pulmonary ventilator of claim 4, wherein the operation of the ventilator through the phases of the cycle does not require the application of any energy beyond that provided by the pressure of the gas entering the ventilator through the gas inlet.

6. A mini pneumatic mechanical pulmonary ventilator comprising:

a) a diaphragm including an outer edge, a flexible lateral part within the outer edge, and a ring-shaped salience formed on a first side of the diaphragm;

b) a spring within a chamber for applying pressure on a second opposing side of the diaphragm;

c) a gas inlet and a gas outlet, the gas inlet adapted to receive gas pressurized above ambient atmospheric pressure, d) a pathway in fluid connection with the gas inlet when the diaphragm moves toward the chamber;

e) a needle valve in fluid communication with the pathway and cooperating with a opening to allow some of the gas to leak past the needle valve and enter the chamber; and f) wherein in a first cycle phase:

gas entering the ventilator through the gas inlet applies pressure to the first side of the diaphragm within the ring shaped salience and the pressure of the gas entering the ventilator from the gas inlet is sufficient to overcome the pressure of the spring and moves the diaphragm toward the chamber, opening the pathway for the gas to pass beyond the diaphragm and toward the gas outlet and the needle valve, the pressure of the gas leaking into the chamber acts on the second side of the diaphragm and adds to the pressure being applied to the second side of the diaphragm by the spring until the pressure on the second side of the diaphragm is sufficient to move the diaphragm away from the chamber, blocking the pathway and holding the incoming gas from passing the diaphragm, the length of the first cycle phase defined as a period of time when the pathway is closed to gas from the gas inlet; and in a second cycle phase:

the gas within the chamber leaking past the needle valve out of the chamber into the passageway, reducing the pressure in the chamber until the pressure of the incoming gas within the ring-shaped salience on the first side is sufficient to move the diaphragm toward the chamber and allow gas from the gas inlet to enter the pathway the length of the second cycle phase defined as a period of time when the pathway is open to gas from the gas inlet;

g) the first and second phases together defining a cycle.

* * * * *

UNITED STATES PATENT AND TRADEMARK OFFICE
CERTIFICATE OF CORRECTION

PATENT NO.   : 6,431,169 B1                                                    Page 1 of 1
DATED        : August 13, 2002
INVENTOR(S)  : Do Val et al.

It is certified that error appears in the above-identified patent and that said Letters Patent is hereby corrected as shown below:

Drawings,
Sheet 38 of 40, (Fig. 38), delete the legend "PRIOR ART"
Sheet 39 of 40, (Fig. 39), delete the legend "PRIOR ART"

Column 7,
Line 49, "the incoming gas" should read -- incoming gas --
Lines 52-53, "the incoming gas" should read -- incoming gas --
Line 65, both occurrences, "the frequency" should read -- frequency --

Column 8,
Line 3, "the amount" should read -- an amount --
Line 6, "the adjusting the depth" should read -- adjusting a depth --
Line 52, "the incoming gas" should read -- incoming gas --
Lines 52-53, "the length" should read -- a length --
Line 57, "the passageway" should read -- the pathway --
Line 60, "the incoming gas" should read -- incoming gas --
Line 63, "the length" should read -- a length --

Signed and Sealed this

Tenth Day of June, 2003

JAMES E. ROGAN
*Director of the United States Patent and Trademark Office*